(12) United States Patent
Jestrabek-Hart

(10) Patent No.: US 6,470,886 B1
(45) Date of Patent: Oct. 29, 2002

(54) CONTINUOUS POSITIVE AIRWAY PRESSURE HEADGEAR

(75) Inventor: Bernadette Jestrabek-Hart, Meridian, ID (US)

(73) Assignee: Creations by B J H, LLC, Meridian, ID (US)

( * ) Notice: Subject to any disclaimer, the term of this patent is extended or adjusted under 35 U.S.C. 154(b) by 0 days.

(21) Appl. No.: 09/536,002

(22) Filed: Mar. 23, 2000

Related U.S. Application Data

(60) Provisional application No. 60/125,744, filed on Mar. 23, 1999.

(51) Int. Cl.⁷ .............................................. A62B 18/08
(52) U.S. Cl. .............................. 128/207.11; 128/207.13; 128/207.17
(58) Field of Search ........................ 128/206.13, 206.27, 128/207.11, 207.13, 207.17, 207.18

(56) References Cited

U.S. PATENT DOCUMENTS 2,292,568 A   8/1942   Kanter et al. ................ 128/198

(List continued on next page.)

FOREIGN PATENT DOCUMENTS

| DE | 380559 | * | 9/1923 | ............ 128/207.11 |
| EP | 0549299 A | * | 6/1993 | ............ 128/207.18 |
| FR | 971.409 | * | 7/1950 | ............ 128/207.11 |
| GB | 861574 | * | 2/1961 | ............ 128/207.11 |

OTHER PUBLICATIONS

U.S. Department of Health and Human Services, Public Health Service, National Institutes of Health, Publication No. 95–3798, Sep. 1995.

Primary Examiner—Aaron J. Lewis
(74) Attorney, Agent, or Firm—Ken J. Pedersen; Barbara S. Pedersen

(57) ABSTRACT

The present invention is a CPAP Headgear for assisting in the treatment of sleep apnea. The present invention uses a standard CPAP respiratory mask with air supplied under pressure by an air blower or other source. The present invention generally includes an improved Headgear, preferably having a head cover, a Lip Strap, and Clips and/or Extenders to hold the CPAP respiratory mask in place. The head cover designed with two side portions, each encircling an ear with an open area where the ear will fit and thereby stay a distance from the ear with material that goes upwards toward the top of the head, one side separating into 2 straps that connect across the top of the head to the second side. Another strap comes from the back of the left side that encircles the ear and around the nape of the neck to the right side that encircles the right ear, up and through, and back over toward the left, connecting upon itself, thereby connecting the two headpieces together across the nape of the neck. The Lip Strap extends from both lower sides in front of the ears and is attached from one side of the Headgear to the other, and is placed below and on the lower lip cooperating to help keep the wearer's lower lip against the teeth, thereby inhibiting the escape of air from the wearer's mouth, while allowing the chin to relax, and allowing the teeth to be apart as the wearer sleeps. The Clip is a bent hook that attaches to the side strap from the headgear to the respiratory mask attachment and allows the headgear to be removed and replaced easily without losing the adjustments. The Extenders are attachments that are part of a mask or can be or a bent wire attached to an existing respiratory mask. The Extenders drop/lower the attachment where the Headgear is to fasten to the respiratory mask to an area blow the mask. The Extenders primary function is to make the respiratory mask more comfortable to wear, and they may take the place of the Clip. The open Extender allows the Headgear to be removed and replaced easily without losing adjustments.

14 Claims, 12 Drawing Sheets

U.S. PATENT DOCUMENTS

| | | | | |
|---|---|---|---|---|
| 2,353,643 A | | 7/1944 | Bulbulian | 128/141 |
| 4,406,283 A | | 9/1983 | Bir | 128/207.18 |
| 4,412,537 A | * | 11/1983 | Tiger | 128/207.13 |
| 4,739,757 A | | 4/1988 | Edwards | 128/207.18 |
| 5,038,776 A | * | 8/1991 | Harrison et al. | 128/207.11 |
| 5,269,296 A | * | 12/1993 | Landis | 128/207.18 |
| 5,284,469 A | | 2/1994 | Jasen | 602/17 |
| 5,361,416 A | | 11/1994 | Petrie et al. | 2/171 |
| 5,429,683 A | * | 7/1995 | Le Mitouard | 128/207.11 |
| 5,542,128 A | * | 8/1996 | Lomas | 128/207.11 |
| 5,640,974 A | | 6/1997 | Miller | 128/845 |
| 5,653,228 A | | 8/1997 | Byrd | 128/207.11 |
| D383,204 S | | 9/1997 | Lomas | D24/110 |
| 5,687,715 A | | 11/1997 | Landis et al. | 128/207.18 |
| 5,687,743 A | | 11/1997 | Goodwin | 128/848 |
| 5,704,916 A | | 1/1998 | Byrd | 604/179 |
| 5,724,965 A | | 3/1998 | Handke et al. | 128/207.13 |
| 6,112,746 A | * | 9/2000 | Kwok et al. | 128/207.13 |
| 6,119,693 A | * | 9/2000 | Kwok et al. | 128/207.11 |
| 6,119,694 A | * | 9/2000 | Correas et al. | 128/207.18 |

\* cited by examiner

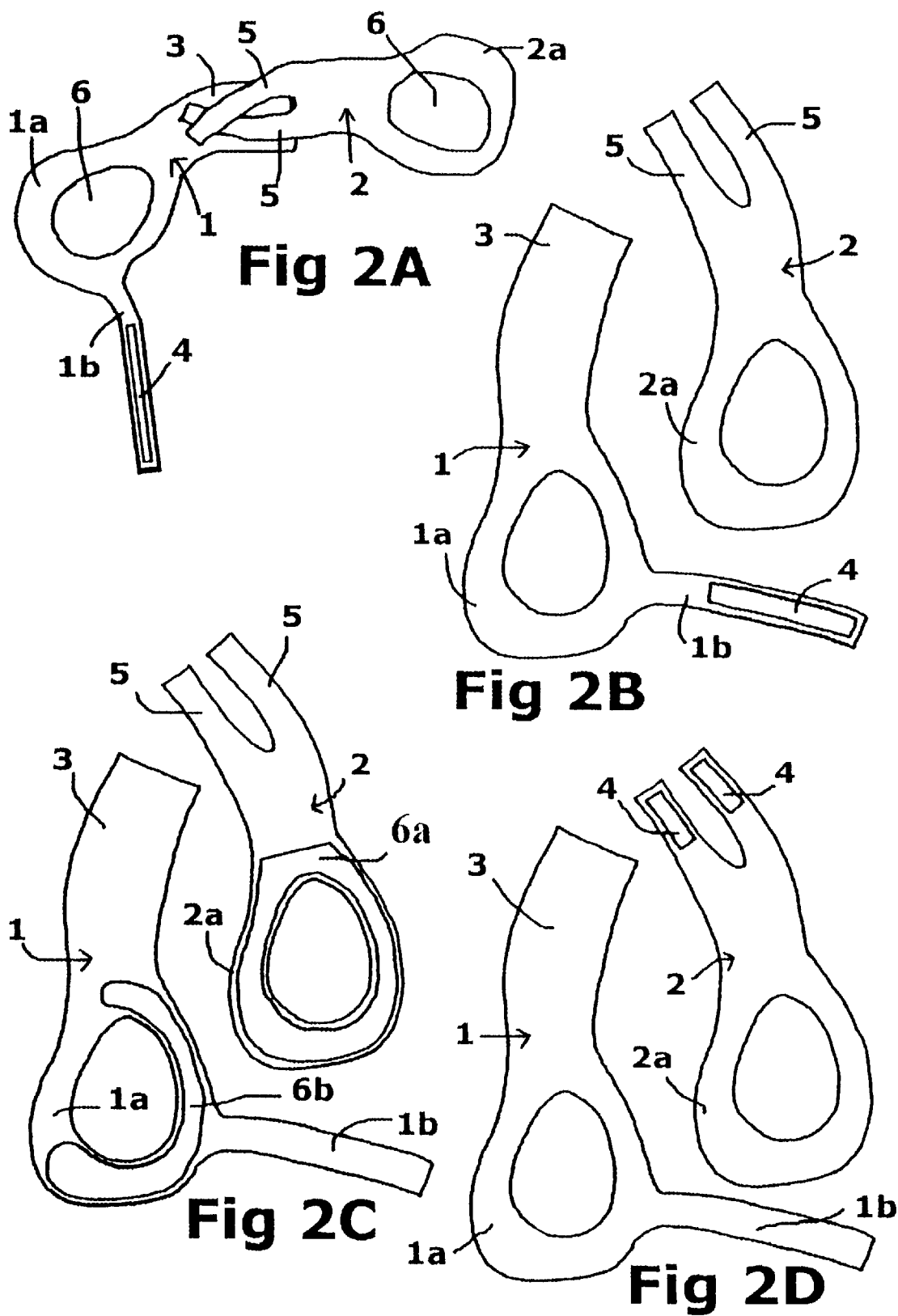

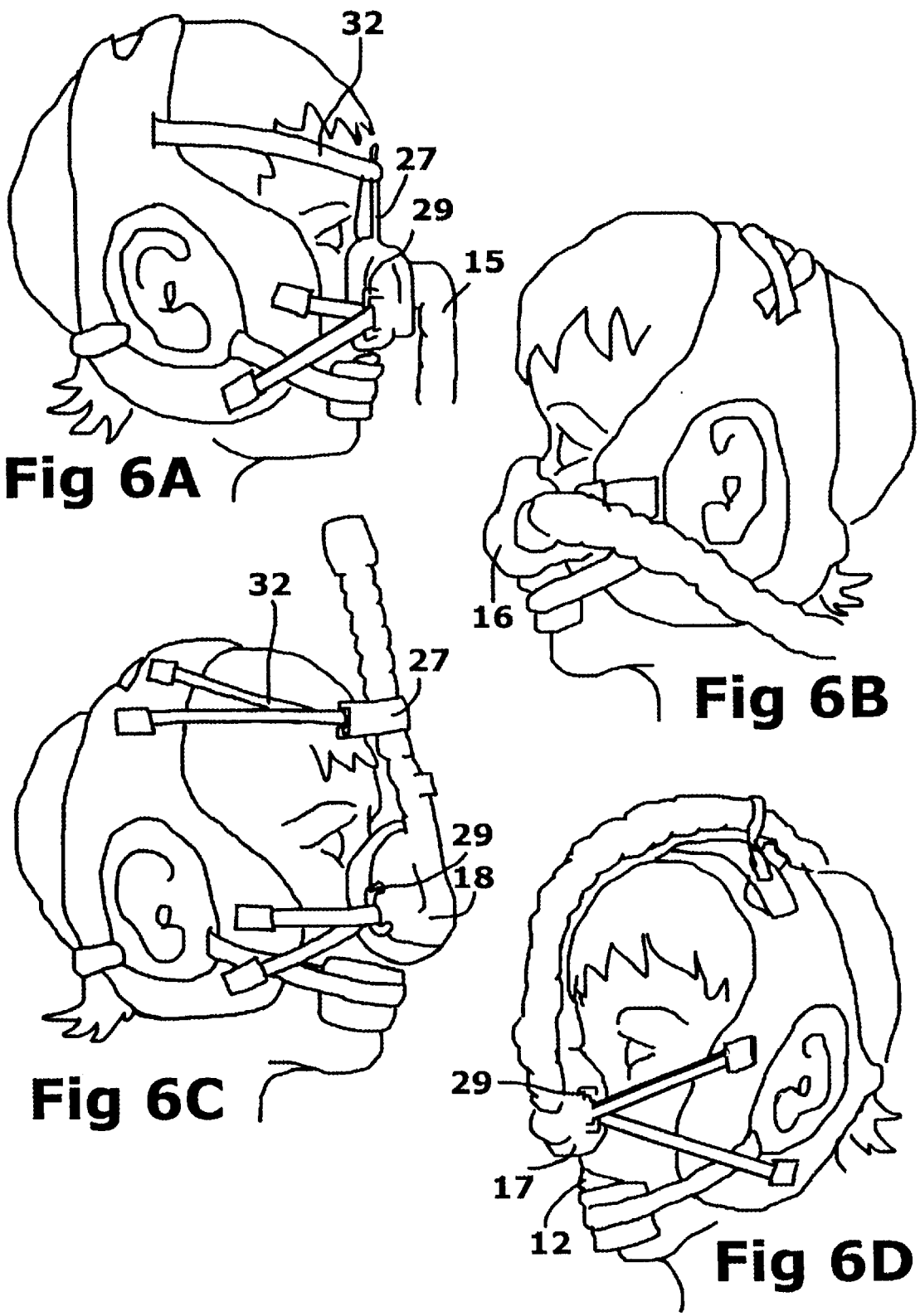

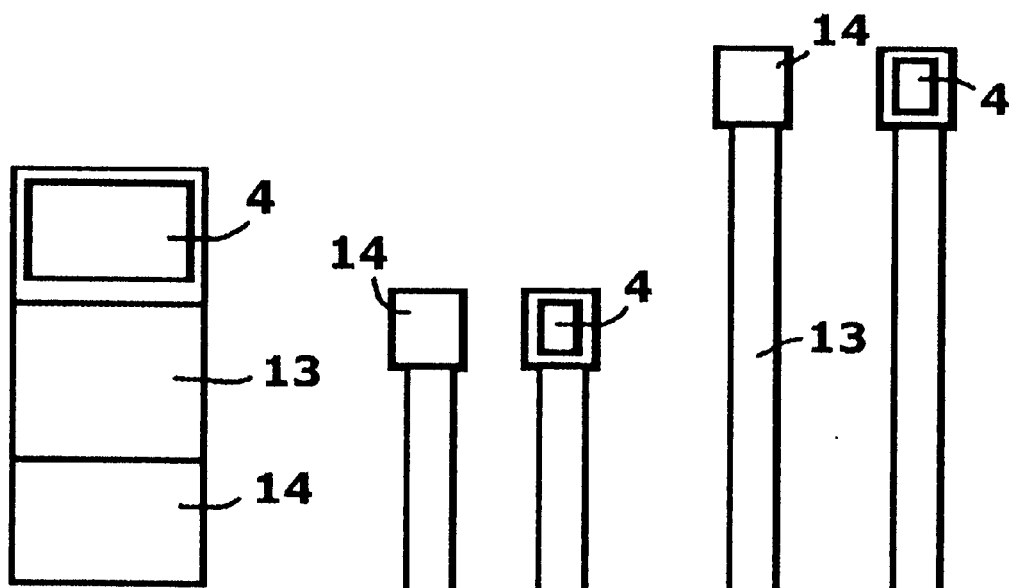
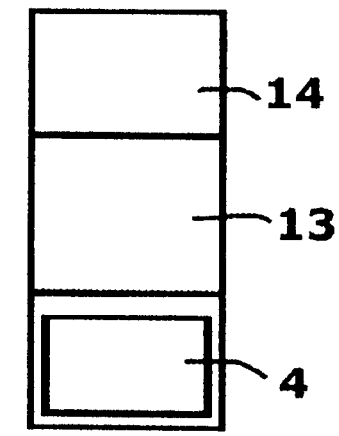
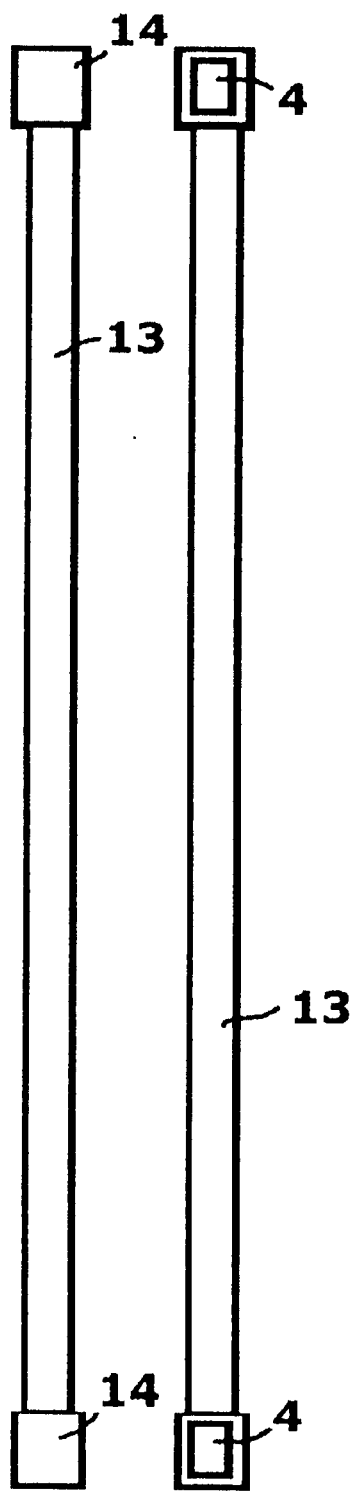
Fig 7A
Fig 7B
Fig 7C
Fig 7D
Fig 7E

CONTINUOUS POSITIVE AIRWAY PRESSURE HEADGEAR

DESCRIPTION

This application claims priority of my prior, co-pending provisional patent application, Ser. No. 60/125,744, filed Mar. 23, 1999, entitled "Head Gear for Treating Sleep Apnea," which is incorporated herein by reference.

BACKGROUND OF THE INVENTION

1. Field of the Invention

The present invention generally relates to medical equipment. More specifically, the present invention relates to headgear used in the treatment of sleep apnea.

2. Related Art

Sleep apnea is a breathing disorder characterized by brief interruptions of breathing during sleep. Certain mechanical and structural problems in the airway of a person cause the interruptions in breathing during sleep. In some people, apnea occurs when the throat muscles and tongue relax during sleep and partially block the opening of the airway. When the muscles of the soft palate at the base of the tongue and the uvula (the small fleshy tissue hanging from the center of the back of the throat) relax and sag, the airway becomes blocked, making breathing labored and noisy and even stopping it all together. Sleep apnea also can occur in obese people when an excess amount of tissue in the airway causes it to be narrowed. With a narrowed airway, the person continues his or her efforts to breathe, but air cannot easily flow into or out of the nose or mouth. Unknown to the person, this results in heavy snoring, periods of no breathing, and frequent arousals (causing abrupt changes from deep sleep to light sleep). Source: Facts About Sleep Apnea, National Institute of Health, Publication No. 95-3798, September 1995.

During the apneic event, the person is unable to breathe in oxygen and to exhale carbon dioxide, resulting in low levels of oxygen and increased levels of carbon dioxide in the blood. The reduction in oxygen and increase in carbon dioxide alert the brain to resume breathing and cause an arousal. With each arousal, a signal is sent from the brain to the upper airway muscles to open the airway; breathing is resumed, often with a loud snort or gasp. Frequent arousals, although necessary for breathing to restart, prevent the patient from getting enough restorative, deep sleep. Id.

Nasal continuous positive airway pressure (CPAP) is the most common effective treatment of sleep apnea. In this procedure, the patient wears a respiratory mask over the nose during sleep, and pressure from an air blower forces air through the nasal passages. The air pressure is adjusted so that it is just enough to prevent the throat from collapsing during sleep. The pressure is constant and continuous. Nasal CPAP prevents airway closure while in use, but apnea episodes return when CPAP is stopped or used improperly. Id.

Variations of the CPAP device attempt to minimize side effects that sometimes occur, such as nasal irritation and drying, facial skin irritation, abdominal bloating, mask leaks, sore eyes, and headaches. Id.

One device for the treatment of sleep apnea is shown in U.S. Pat. No. 5,361,416 (Petrie et al.). The Petrie et al. device comprises a head cover and chin strap for treating sleep apnea. However, the Petrie et al. device is not a CPAP device.

Another device, this one for the reduction of snoring activity, is shown in U.S. Pat. No. 5,687,743 (Goodwin). The Goodwin device comprises a head strap assembly for reducing snoring activity. However, the Goodwin device is also not a CPAP device.

Another device, this one for a Nasal Mask and a headgear, is shown in U.S. Pat. No. 5,724,965 (Respironics Inc.). The Respironics Inc. device comprise a respiratory mask and the headgear to hold this respiratory mask in place. This Respironics Inc. device is a CPAP device.

SUMMARY OF THE INVENTION

The present invention is a CPAP headgear for assisting in the treatment of sleep apnea. The present invention may use a standard CPAP respiratory mask supplied with air under pressure by an air blower or other source. The present invention generally comprises an improved Headgear, preferably having a Lip Strap, and a Clip or Extenders and the ability to attach to and hold the CPAP respiratory mask in place.

The Headgear is specifically designed with two side portions, which are preferably separate panels with various sections for proper connection to each other and to the wearer. Each side portion encircles an ear with an open area where the ear will fit and thereby stay a distance from the ear with material that goes upwards toward the top of the head. One side separates into two straps near the top that connect across the top of the head to the second side. Another strap extends from the back of the left side piece that encircles the ear and around the nape of the neck to the right side that encircles the right ear and back over toward the left, connecting upon itself. With these various attachments of the two side panels to each other, the two pieces of the head cover are connected over the top of the head and also connected together across the back of the neck. This feature of not putting pressure on or touching the ears of the wearer adds a great level of comfort to the CPAP apparatus.

The present invention preferably also has a Lip Strap. The Lip Strap extends from and is attached to a first front lower side of the Headgear, wraps around the user's head at a location under and over the user's lower lip, and extends and attaches to a second lower front side of the Headgear. The Lip Strap needs to be snug, but not tight against this location, thereby keeping the lower lip against the teeth and thereby disallowing air to escape from the user's mouth. The teeth may be in a relaxed and open position and the Lip Strap will still disallow the air to escape from the user's mouth. The use of such a Lip Strap is preferred, but optional.

The main problems with prior CPAP headgears which are overcome in the present invention include: the prior art CPAP headgears are uncomfortable to wear, especially when the headgear slip or rides up on the wearer's head, hurting the wearer's ears; and the prior art CPAP headgears do nothing to force the user to breathe through the user's nose, thereby resulting in a dry mouth when the user awakens the next morning. This head cover, made of two pieces, one for each side of the head, encircle the ears with a hole in the middle that is placed over the ears and is large enough as not to touch the ears. The side pieces extend upward to the top of the head and connect to each other across the top of the head. The side pieces also extend around and connect at the nape of the neck thereby keeping the Headgear in place.

The preferred material is also an important component that keeps the Headgear in place. Another benefit of the present invention over prior CPAP headgears, is the non-elastic and still flexible characteristic of the preferred material of manufacture, in comparison to the stretchy plastic and/or elastic used in many of the prior art articles. Being non-elastic and still flexible allows the present invention to firmly hold the user's head without becoming too tight, which is a major problem of the prior art articles. The preferred two headgear panels have substantially continuous inner surfaces except for the apertures that receive the ears, that is, broad and gentle surfaces for increased comfort compared to the lack of comfort typical of narrow straps or ties. The preferred material of manufacture also allows for the hook side of a hook and loop type fastener to attach anywhere on the outside of this Headgear which allows a multitude of adjustment possibilities.

Another problem with prior CPAP headgears which is overcome in the present invention includes: the prior art CPAP headgears are difficult to take off and put back on without loosening the straps that attach to the respiratory mask and thereby losing the adjustment, especially when one has to un-attach the straps holding the respiratory mask each time one removes the respiratory mask. The Clip is a bent hook made of plastic or metal that connects to the side elastic strap on one side of the headgear and attaches to the respiratory mask and allows the removal without loosening the straps that hold the respiratory mask in place. The open extender is on one side and either part of the respiratory mask or is a bent wire that is attached to the respiratory mask and can be used for this same purpose as the Clip.

Another problem with prior CPAP headgears which is overcome in the present invention includes: the prior art CPAP headgears attach to the respiratory mask in the area near the nose or the center part of the respiratory mask. When attaching in this area, the respiratory mask needs a lot of pressure against the face to keep the air from leaking from the respiratory mask that is next to the face. This also, usually requires a piece that attaches to the respiratory mask and goes above the nose, between and above the eyes and usually then has a part that rests against the face near or above and between the eyebrows.

Extenders can either be made of strong plastic and be made as part of the respiratory mask or they can be made separately and attach to an existing respiratory mask. Extenders that are part a respiratory mask are plastic hooks that are positioned below the mask and with one side having a closed hook and the other side an open hook through which the side straps of a headgear are fastened. Extenders that are additional to an existing respiratory mask are made of a strong and lightweight metal that on the upper end have a bent open circle which will fasten, when closed, to the existing mask attachment where the strap usually attaches and the lower end to be bent in a closed hook on one Extender and with an open hook on the other Extender, to which the side straps of the Headgear will fasten. This will drop the area to which the Headgear straps attach to the respiratory mask below the nose and mask. In addition to the open Extender making it easy to take the Headgear off and on, the lowering of the attachment the Extenders give to the ability to keep the respiratory mask in place without needing as much pressure against the face, and they keep the respiratory mask away from the eyebrow and forehead area. They do this by dropping the attachment below the nose and mask which then positions the part of the respiratory mask that is above the nose slightly away from the face in the eyebrow area and still allows the respiratory mask air to seal and not allow air to escape where it is against the face. By lowering the attachment area, as the extenders do, seems to not require that the mask have as much pressure against the face and still keep the air from leaking from the respiratory mask that is next to the face.

BRIEF DESCRIPTION OF THE DRAWINGS

FIGS. 2A–D are views showing the pattern of the Headgear, outside, inbetween, and underside and showing the two parts of the Headgear attached of the preferred embodiment.

FIGS. 6A–D are perspective views of different respiratory masks and illustrate ways to attach their different respiratory masks to the Headgear embodiment.

FIGS. 7A–E are perspective views of the straps needed when attaching various respiratory masks to the preferred embodiment.

DESCRIPTION OF THE PREFERRED EMBODIMENTS

Figure 1A:
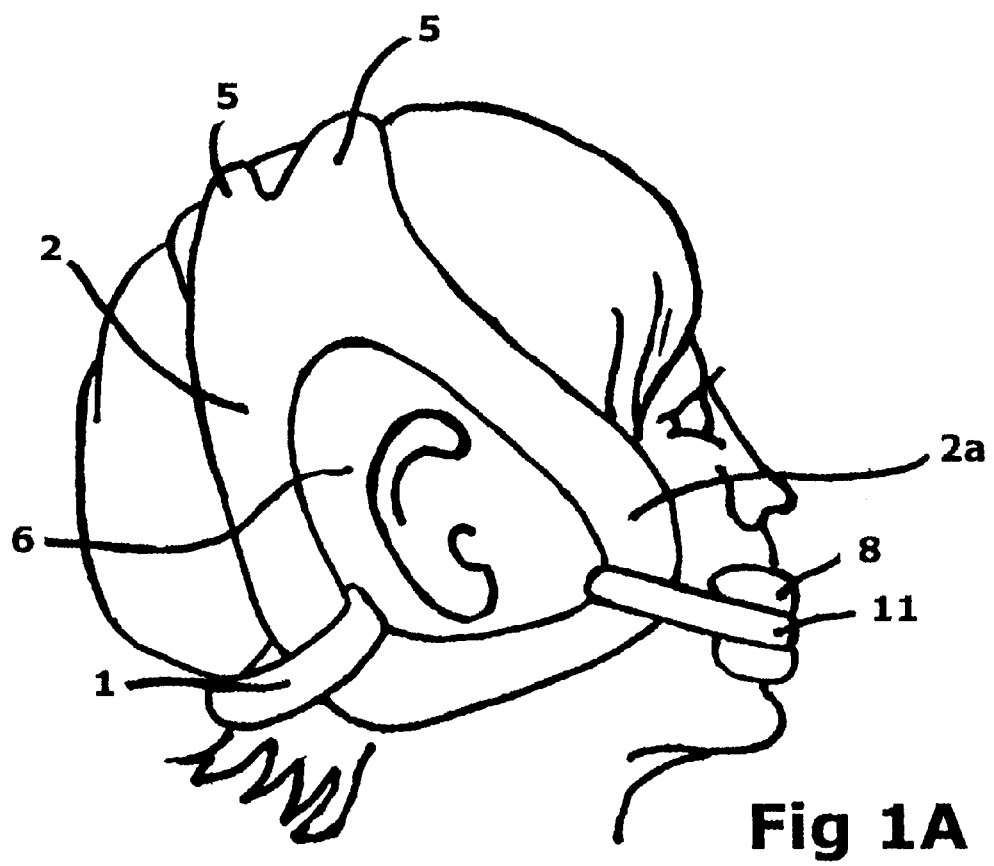
FIGS. 1A–B are views showing the complete Headgear, and Lip Strap of the preferred embodiment of the present invention.
Figure 1B:
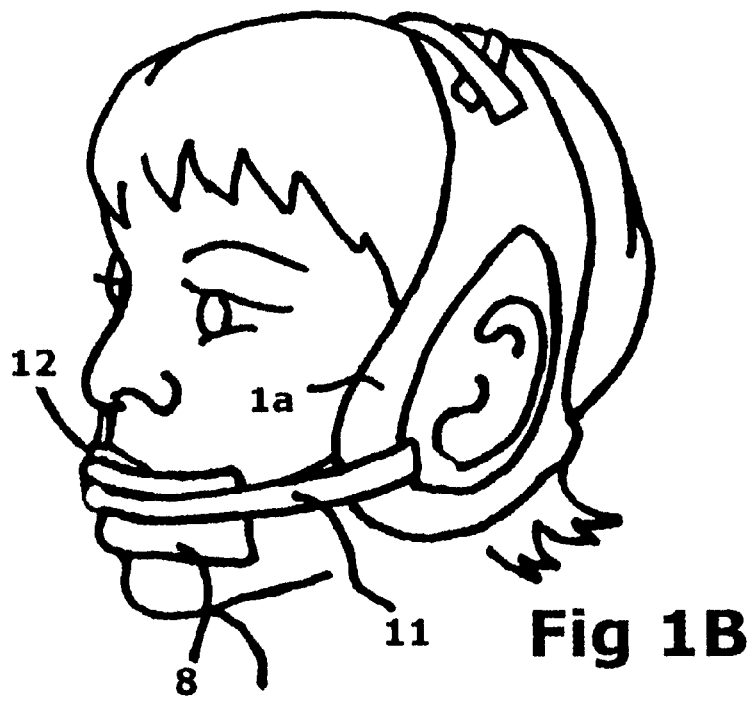

As shown in the Figures, particularly FIGS. 1A–B, and FIGS. 6A–D, the present invention is a CPAP headgear for assisting in the treatment of sleep apnea. The preferred embodiment of the present invention is shown in FIGS. 1A–B and comprises a head cover FIGS. 1A–B, FIGS. 2A–D, a lip strap FIGS. 1A–B, 4A–D, and 5A–E and if used to attach a respiratory mask, FIGS. 6A–D, & 7A–E, or Extenders, FIGS. 8, 9, 10A–C, 11C, & 13. When the Headgear is used to attach a respiratory mask, it is preferable to use a Clip 23, see FIGS. 14A–C. 15, & 16, a suggested addition embodiment, or Extenders, see FIGS. 8A–C. 9, 10A–C, 11A–C & 13, another suggested additional embodiment of the present invention, which allow both quick removal of the Headgear and make the respiratory more comfortable.

The head cover preferably comprises a soft, flexible cloth or other underside surface, pleasant to the touch, and a material that will not stretch FIG. 2D, and is the part that will lay next to the head. The head cover outside, see FIG. 2B, preferably comprising a soft flexible foam having a cloth or other outside surface, and a material that the hook side of a hook and loop fastener will be able to receive and will attach. Use of such an adjustable fastener allows the present invention to more easily be adjusted to fit the heads of different people.

On both sides or "panels" 1 & 2, sewn inbetween these two materials, see FIG. 2C, is a piece of plastic in the suggested design shape as 6a, which encircles the ears, or 6b, which goes from the back of the ear and under the ear to the front 1a, of the Headgear. This plastic piece allows the Headgear to keep its shape and withstand the pressure put against it.

Figure 3A:
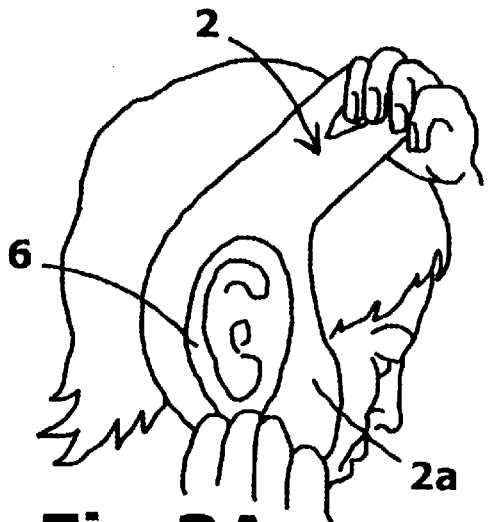
FIGS. 3A–E are views how to put the two parts of the headgear embodiments together and fit them onto the head of the wearer.
Figure 3B:
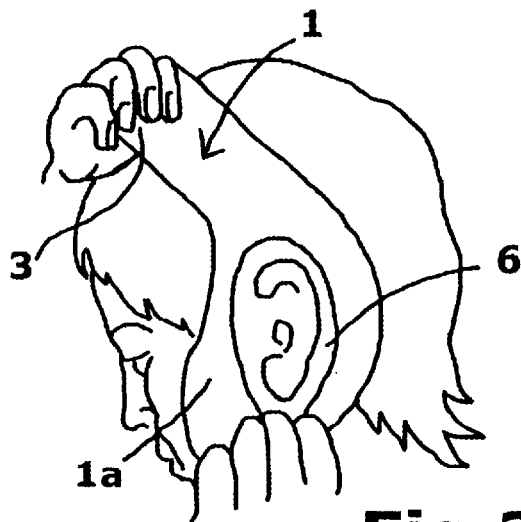
Figure 3C:
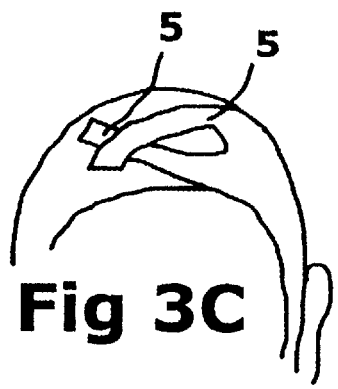
Figure 3D:
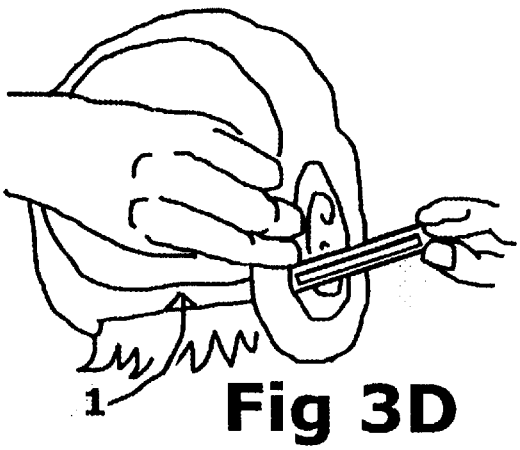
Figure 3E:
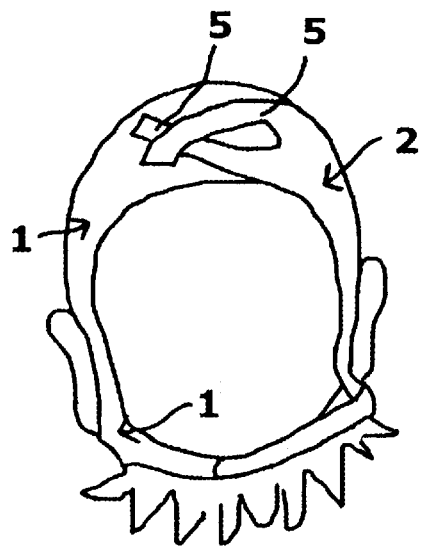
Figure 4A:
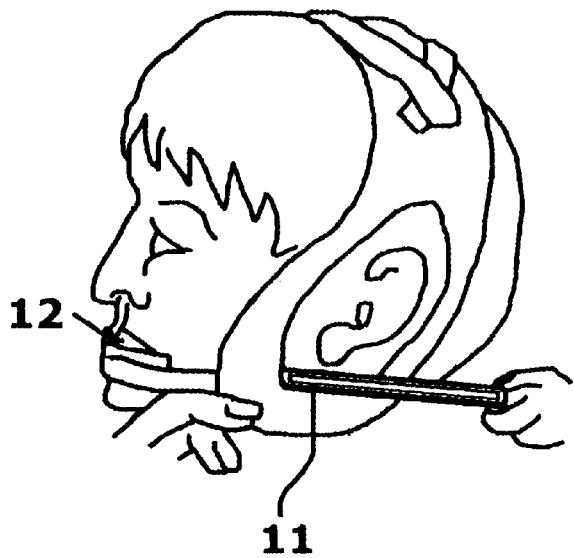
FIGS. 4A–D are perspective views showing how to place the Lip Strap embodiment on the wearer's head.
Figure 4B:
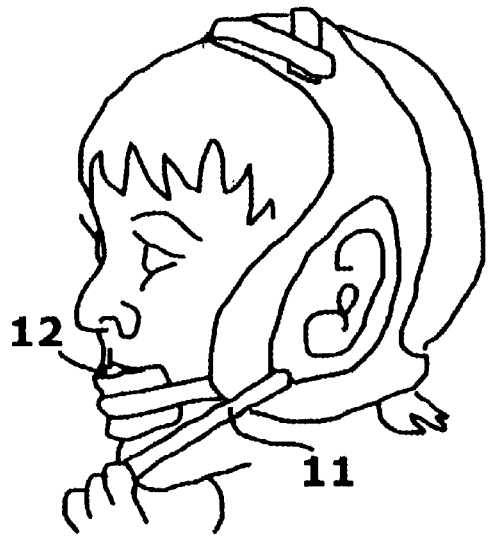
Figure 4C:
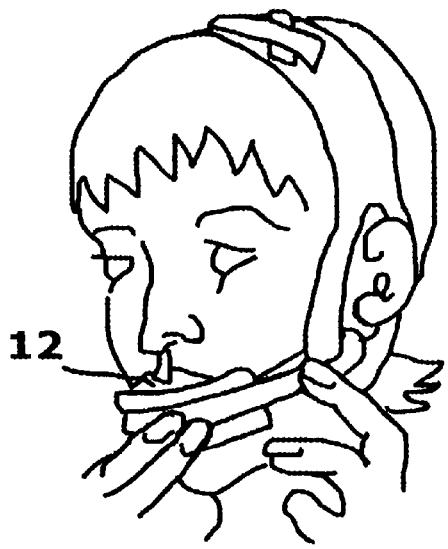
Figure 4D:
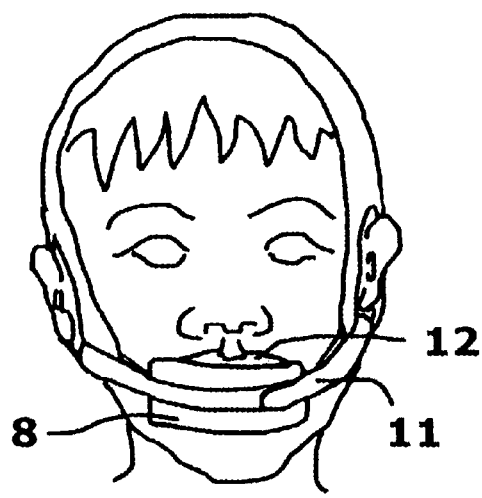
Figure 5C:
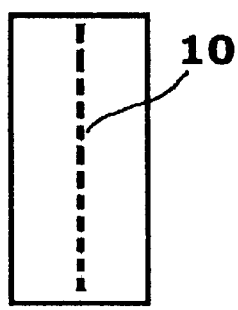
FIGS. 5A–E are views showing the pattern of the Lip Strap embodiment.
Figure 5B:
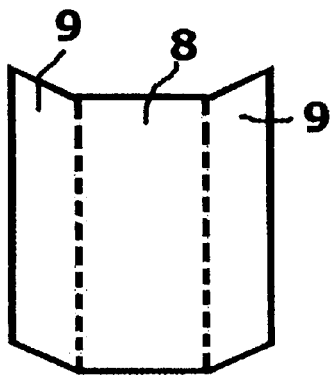
Figure 5A:
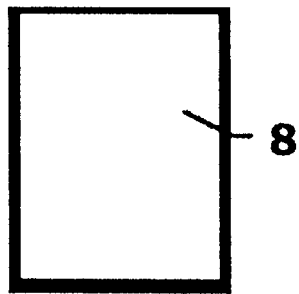
Figure 5D:
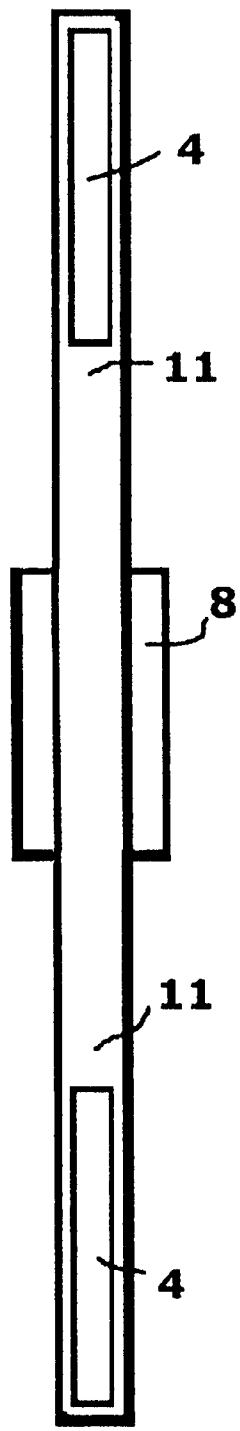
Figure 5E:
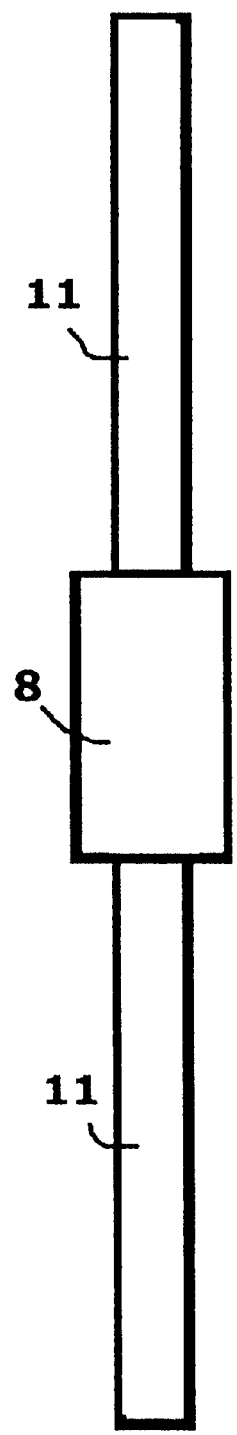

The Headgear 1 & 2 is designed so as it encircles the ears on both sides of the wearer's head and has an open area where the ear is placed. The Headgear that encircles the ears, hereby enveloping, but not covering, the user's ears, and has material 3 & 5 that extend upwards, becoming upwards extensions above the user's ears. These upward extensions extending upwards and over to the portion of the head that is the top of the head, in front of the crown, one side becoming two straps 5, extending over the top of the head and in front of the crown of the wearer's and attaching to the second side in this area, see FIG. 3C. The extension that becomes two straps 5 has the hooked side 4 of a hook and loop type fastener, see FIG. 2D, to allow adjustment on the top 5, see FIG. 2A, to fit and keep it in place around both ears. The headgear also has an extension 1b on the right side of the left section 1 that encircles the left ear to the rear which will go across the nape of the neck 3 and to the section that encircles the right ear and attaches to the left side of that right section, see FIGS. 3A–F, by going under the left side of the right ear section, coming out through the ear hole and back over the right ear section, attaching back onto itself with a hooked side of a hook and loop type fastener. The actual size and dimensions of the pattern will be determined if it is used by a child, small adult or large adult.

The present invention preferably further comprises a Lip Strap, see FIGS. 1A–B, 4A–D, & 5A–E. The preferred Lip Strap comprises an elongate length 11 of preferred material to which the hook side of a hook and loop type fastener 4 is used on each end of the outside part of the Lip Strap, see FIG. 3D. The leather portion 8, see FIGS. 5A–C, comprise of a rectangle piece of leather folded, see FIGS. 5B–C, into shape with the smooth side out and ends folded 9 to the middle 10, see FIG. 5–C. This folded piece with the folded ends 10 facing the strap 11 is then sewn to the center portion of 11 of the Lip Strap, see FIGS. 5D & E. The side, which goes against the lip, see FIG. 5E, does not have the adjustable fastener, such as the hook side of a hook and loop type fastener 4 and is the side that will touch the lower lip. The side, that is not touching the lip, see FIG. 5D, has the adjustable fastener, such as the hook side of a hook and loop type fastener 4 on each end. The outside, see FIG. 5D, of the strap 11 must be of the preferred material that will accept and attach to the hook part of a hook and loop type fastener. The actual size and dimensions of the pattern will be determined if it is used by a child, small adult or large adult.

To attach the Lip Strap to the Headgear, see FIGS. 4A–D, one end of the Lip Strap 11 with the side that has the adjustable fastener, such as the hook side of a hook and loop type fastener 4 faced up, away from the face, goes under the bottom front 2a right side of the Headgear, up through the earhole and back attaching onto itself in front on the Lip Strap 11 with the adjustable fastener such as the hook side of a hook and loop type fastener 4. The Lip Strap leather 8 is placed under and on the bottom lip, barely touching and leaving little or no pressure on the upper lip 12, The other end of the Lip Strap 11 with the side that has the adjustable fastener, such as the hook side of a hook and loop type fastener 4 faced up, away from the face, goes under the bottom front of the left side 1a, up through the left earhole and back and attaching onto itself with the adjustable fastener, such as the hook side of a hook and loop type fastener 4 in front on the Lip Strap.

The leather portion 8 of the Lip Strap keeps the user's lower lip against the teeth and thereby helping keep air from escaping from the user's mouth, even if the teeth are slightly apart and the chin is relaxed.

The wearer has the option of wearing the Headgear to only use the Lip Strap and uses another Headgear to attach the respiratory mask or can use this Headgear to attach both the Lip Strap and a respiratory mask.

This Headgear can be used to attach the respiratory mask with the addition of elastic straps 13, see FIGS. 7A–D. The side mask attachment strap, see FIG. 7A–D, comprises a length of elastic material 13, having an adjustable fastener 4 such as the hook side of a hook and loop type fastener 4 attached to each end of the mask attachment strap on the underside and a preferred material to which the hook side of a hook and loop type fastener 4 will attach 14 on the top side, see FIGS. 7C & D. This allows the first end of the strap 13 to be inserted or looped through the respiratory mask attachment 29, and said first end then being fastened to the lower portion of the 1a and/or 2a below the ear portion of the Headgear, and said second end, at a location level at/or above the ear upon the upward extension 1 & 2. Ultimately, the exact locations of such attachments are dependent upon the comfort and wishes of the wearer, and the type of respiratory mask used, said attachment locations being flexible.

One of the important features of the present invention is, that the exact locations of any of these attachments can be varied depending upon the wishes and physical characteristics of the wearer. If the wearer would be more comfortable with a different strap attachment location, the wearer is free to adjust the attachment location accordingly.

Depending on the style of respiratory mask used, for examples see FIGS. 6A–D, elastic 13 straps with ends that have a preferred material that will accept and attach the hook side of a hook and loop type fastener 14 material on one side and the hook side of a hook and loop type fastener 4 on the other side on each end of the 13 elastic straps are used to attach the respiratory mask to the Headgear.

FIG. 6A illustrates how to attach the Respironics "Gold Seal" respiratory mask. It uses two of the FIG. 7C straps to attach the mask, one strap on each side of the face and one FIG. 7D style of elastic strap to hold the top 27 part of the mask to, and touching the eyebrow/forehead area of the face.

FIG. 6B, illustrates the SleepNet Phantom respiratory mask attached to this headgear with FIG. 7A, top side and FIG. 7B is the underside of the elastic straps used on each side of the face to attach this respiratory mask.

FIG. 6C, illustrates the attachment of the Sullivan "Mirage" respiratory mask. This respiratory mask requires two of the FIG. 7C straps to attach the mask, one on each side of the face and two, see FIG. 7D, style of elastic straps, one on each side to hold the top 27 part of the mask to, and touching the eyebrow/forehead area of the face.

FIG. 6D illustrates the Respironic's "Simplicity" attachment to this headgear. It uses two of the FIG. 7C straps to attach the mask, one on each side of the face and if the wearer wants the intake hose to stay above the head, attaches one 15, double sided hook side of a hook and loop type fastener to the top of the Headgear and the intake hose.

All masks are attached by the use of the elastic straps FIGS. 6A–D length and widths determined by what is needed for each particular mask. The actual Headgear is the same in all cases. Some may require the use of the double sided hooked side of a hook and loop type fastener 15 type fastener. Adjust in all areas shown until Headgear is comfortable and noses piece fits well with no air escaping.

To remove the Headgear without the use of the Clip 23 or open Extender 20 or 22 simply unfasten either side strap and the Lip Strap on the same side and lift the Headgear off the head. Another option is to unfasten the nap of the neck strap 3 and lift the Headgear off the head.

If using the Clip 23 simply, remove the Clip from the respiratory mask attachment and lift the Headgear off the head. When using the open Extender 22 simply remove the elastic strap 13 out of the open Extender and lift the headgear off the head.

Figure 14A:
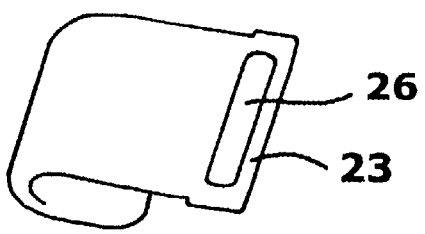
FIGS. 14A–C are perspective views of the Clip, another embodiment of the present invention.
Figure 14C:
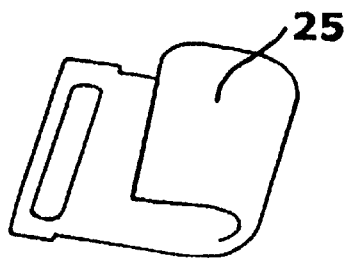
Figure 14B:
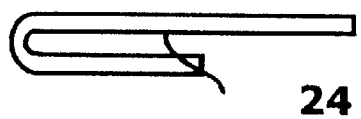
Figure 15:
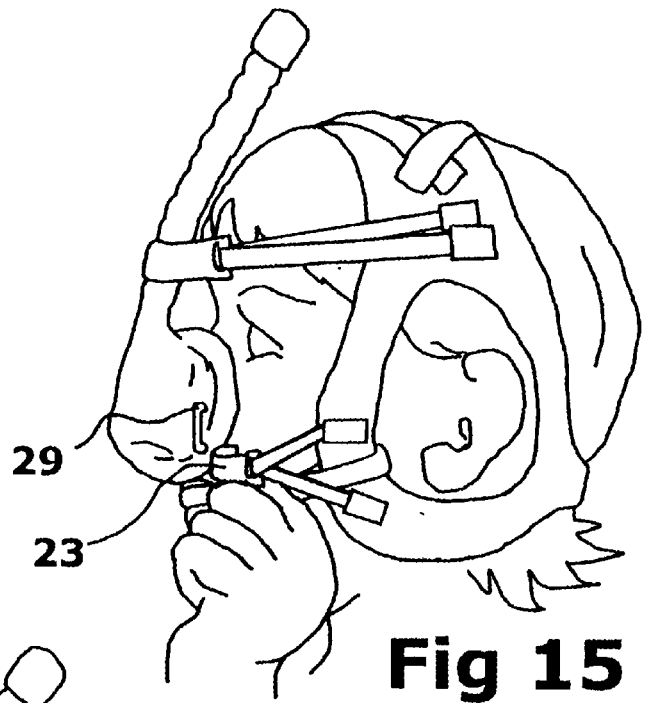
FIG. 15 is a perspective view of how to use the Clip embodiment.
Figure 16:
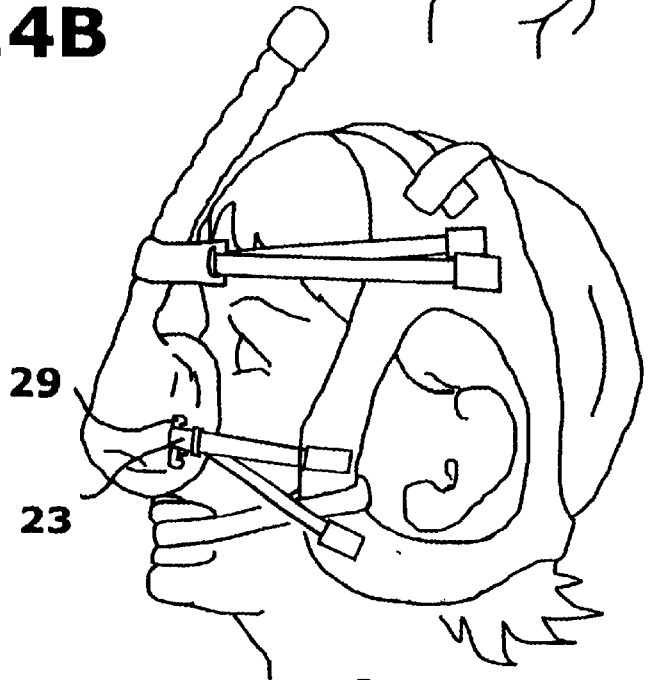
FIG. 16 is a perspective view of the Clip embodiment in place.

An additional embodiment of this invention, making it easier to take the headgear off and on, is the Clip 23, see FIGS. 14A–C. 15 & 16. The preferred Clip 23 comprise a bent hooped shaped piece 24, see top view FIG. 14B, of preferred material being a strong thin plastic or strong, thin and lightweight metal. The size and width is determined by which respiratory mask will be used. The lower end of the standard CPAP respiratory mask attaches to the present invention through the use, of at least one Clip 23, see FIGS. 14A–C. 15 & 16, attached to the elastic strap on the side of the face that is the most convenient for the wearer to use. This Clip 23 affixes to the respiratory mask at the respiratory mask's standard side attachment receiving portion 29, said Clip having the bent end which inserts through said portion 29, and the other end then attaches to the said Headgear by side mask attachment strap 13 insertion of the strap through the opening 26 on the end of the shaped Clip 23. After insertion of elastic strap 13 through the opening 26, then each end of this elastic strap 13 goes back to attach to said Headgear.

The manner in which the present invention is able to attach to a standard mask, is such that it is possible for a wearer to remove or disengage the mask without removing the Headgear. For instance when the user awakes in the night and wishes to leave his or her bed and take a restroom break, talk on the phone, or have something to eat, the wearer can remove the respiratory mask with the use of a Clip 23, or open Extender 20 & 22. The user would merely need to unclip the Clip 23 of the present invention, and push the mask to the side. Or if using the open Extender 22, merely slip the elastic strap from the open Extender 20 or 22 and push the mask to the side. This flexibility allows the user to easily make such a break, without needing to refasten and readjust the Headgear each time, only requiring the user to redo what he/she has undone.

Figure 12:
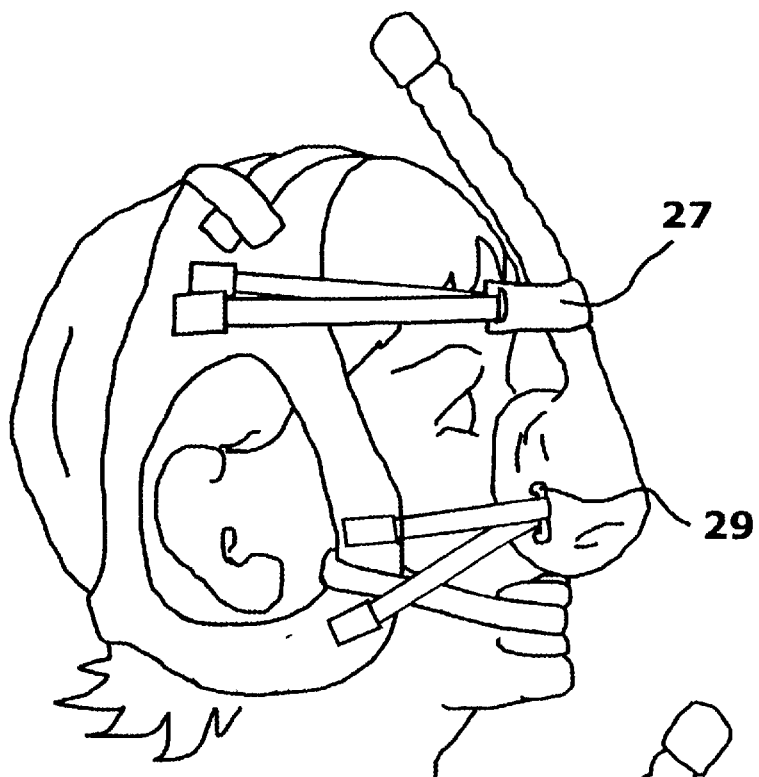
FIG. 12 is a perspective right side view of the Headgear and Lip Strap combination minus the Extenders.
Figure 13:
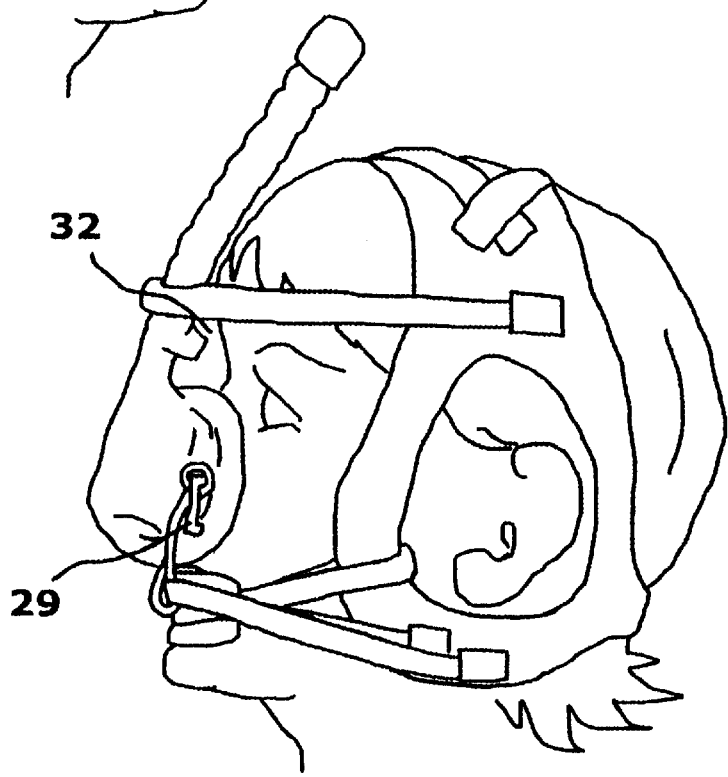
FIG. 13 is a perspective left side view of the Headgear and Lip Strap and the open Extender combination of the embodiments of the present invention.

An additional embodiment of this invention, is Extenders shown in FIGS. 8, 9, 1A–C, 11A–C, & 13. Many of the respiratory masks attach 29 the respiratory mask to the Headgear somewhere in the area to the center of the nose. When attaching in this area, the respiratory mask seems to need a lot of pressure against the face to keep the air from leaking air where the respiratory mask is next to the face. This also, usually requires a piece 27 that attaches to the respiratory mask and goes above the nose, between and above the eyes and usually then has a part that rests against the face near or above and between the eyebrows, see FIGS. 6A, 6C and 12.

Figure 9:
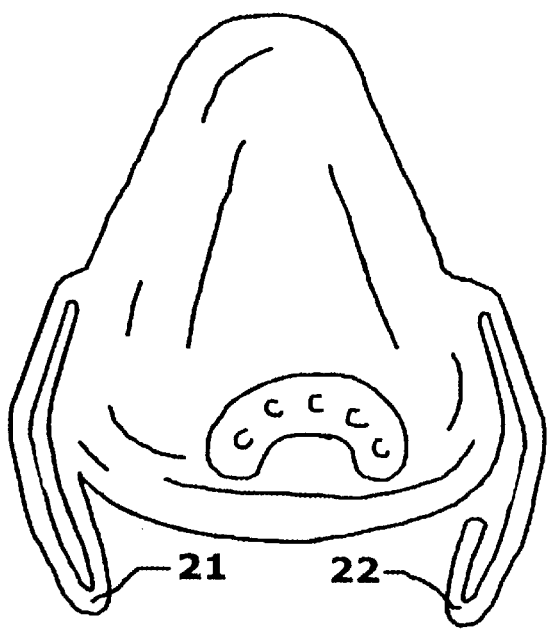
FIG. 9 is a perspective suggested design of the Extenders embodiment that are part of and not an addition to the existing respiratory mask.
Figure 10A:
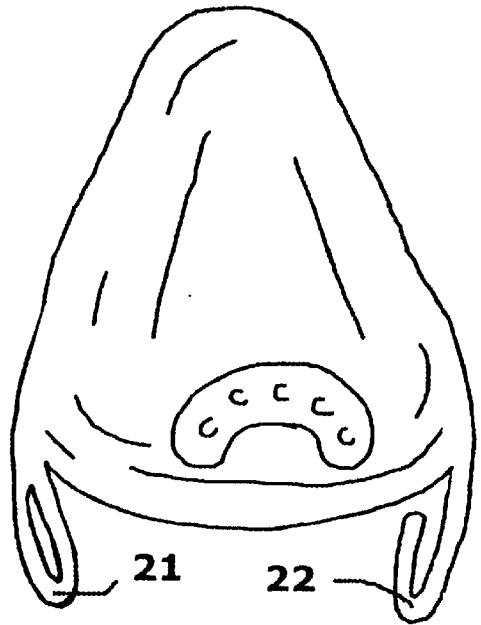
FIGS. 10A–C show another perspective suggested design of the Extenders embodiment if they are part and not an addition to the existing respiratory mask.
Figure 10:
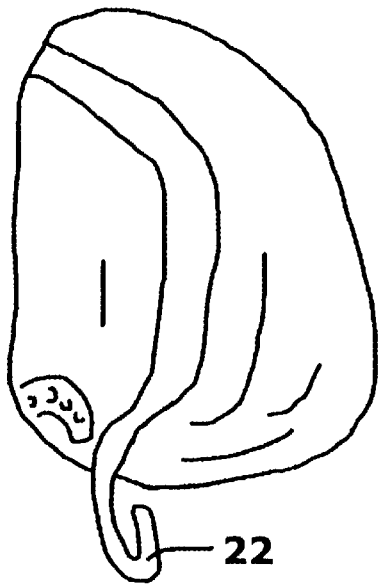
Figure 10C:
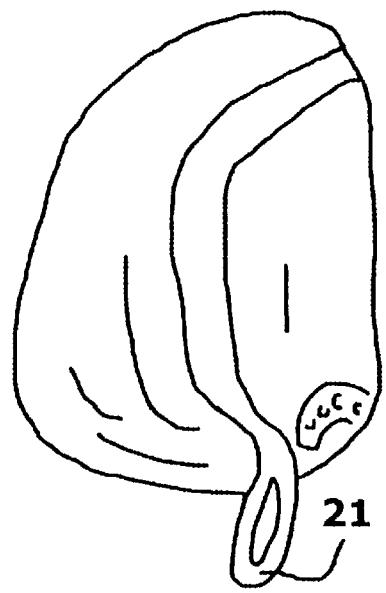
Figure 11A:
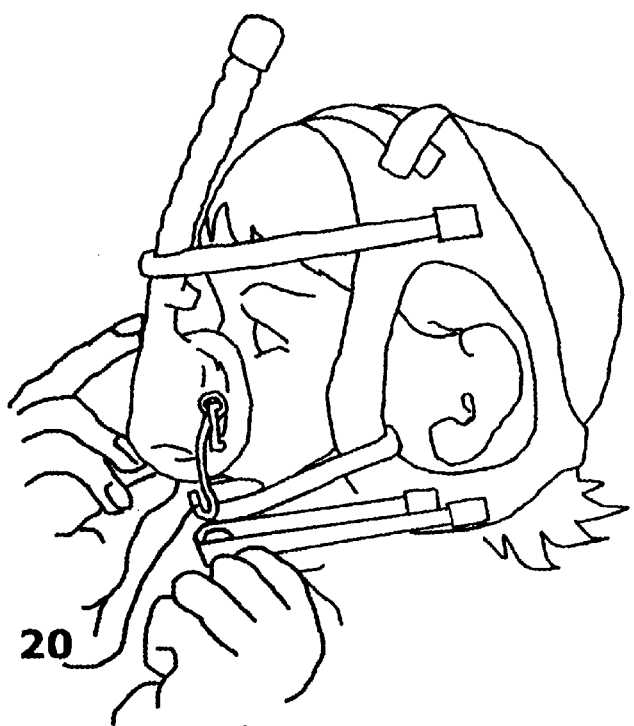
FIGS. 11A–C are perspective views of how to attach the Headgear to the Extenders that are attached as additions to a respiratory mask.
Figure 11B:
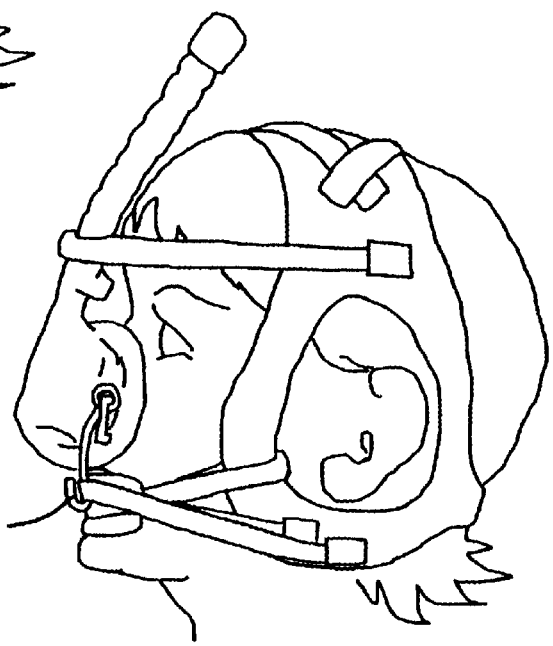
Figure 11C:
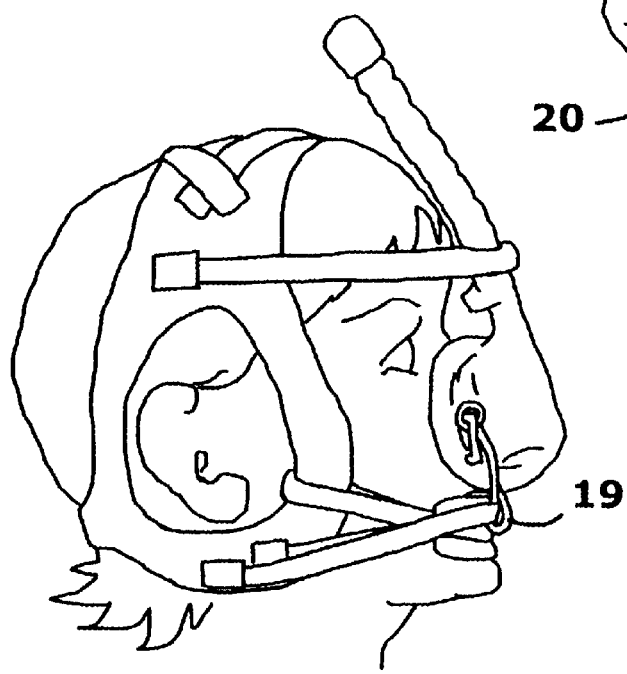

The preferred style of Extenders is made as part of the respiratory mask, see examples 21 & 22 in FIGS. 9 & 10A–C. Extenders that are part a respiratory mask, see FIGS. 9 & 10A–B, are plastic hooks that are positioned below the mask, and with one side having a closed hook 21 and the other side an open hook 22 through which the side straps of a headgear are fastened.

Figure 8A:
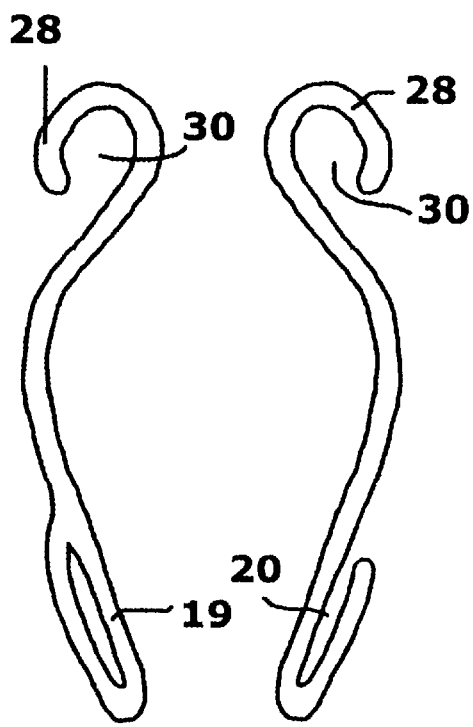
FIGS. 8A–D are perspective views of the Extenders that can be attached as additions to existing respiratory masks and are a suggested part of the embodiment.
Figure 8B:
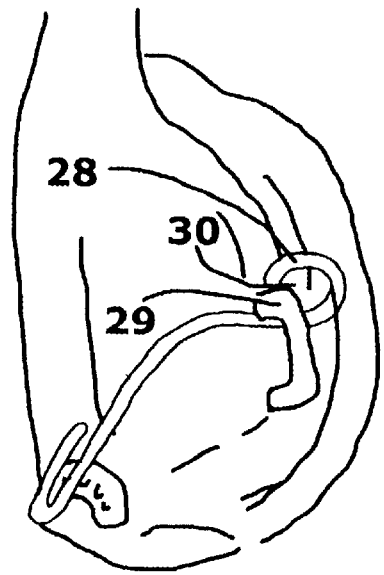
Figure 8C:
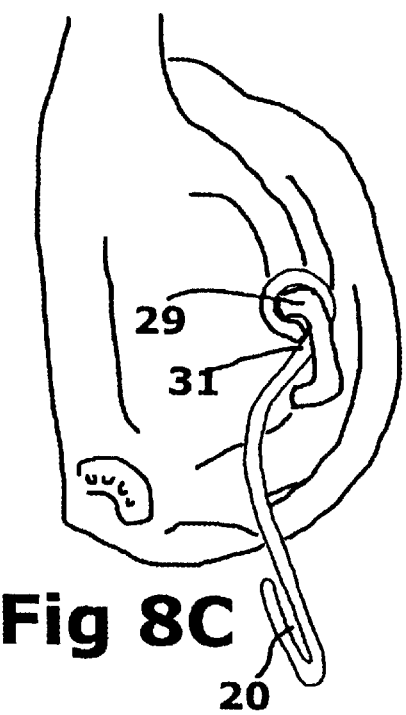
Figure 8D:
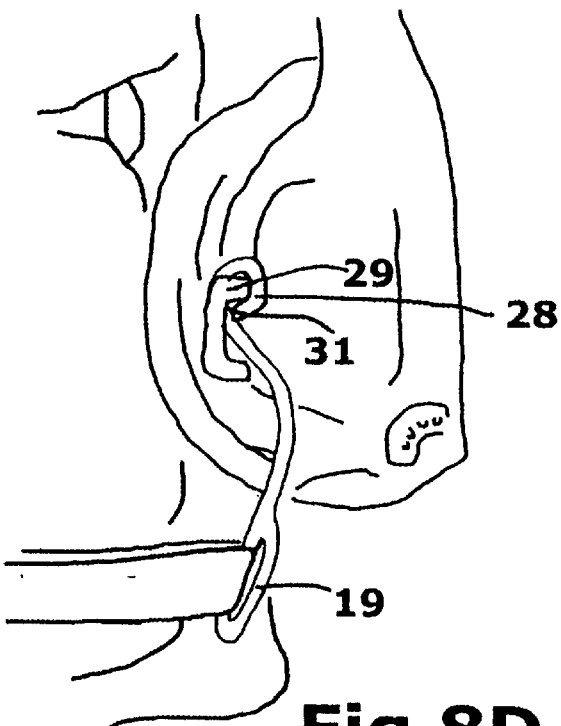

The preferred style of Extender to be used for all respiratory masks that do not have this attachment in their design is one which can be attached to the existing respiratory mask, see FIGS. 8A–C. These are made of a strong and lightweight metal that on the upper end have a bent open 30 circle 28 which will fasten, when closed 31, to the existing mask attachment 29 where the strap usually attaches and the lower end to be bent in a closed hook 19 on one Extender and with an open hook 20 on the other Extender, to which the side straps of the Headgear will fasten. The open Extender will give the ability to quickly unfasten the respiratory mask when needed.

These Extenders are attached to an existing mask by placing the top end 28 through the respiratory mask attachment from the front, over the top of the respiratory mask attachment area see FIG. 8B, and then pinching the area closed 28 against the top attachment area 29 as tightly as possible, see FIG. 8C, with a pliers. The FIGS. 8A–C, show Extenders that are made to have the open extender 20 to be placed on the left side of the wearer's face. If it is more comfortable for the wearer to unhook the Headgear from the right side of the wearer's face, Extenders can be made that have the open extender on the right side.

Both styles of Extenders, see FIGS. 8A–C, 9 & 10A–B change the placement of the pressure of the respiratory mask against the face. These Extenders seem to help keep the mask in place without needing as much pressure against the face and they also keep the respiratory mask away from the eyebrow and forehead area 27. They do this by dropping the attachment below the nose and respiratory mask which then position the part of the respiratory mask that is above the nose, slightly away from the face in the eyebrow area 32, not needing to touch the eyebrow or forehead area of the face, and still allow the respiratory mask air to seal and not allow air to escape where it is against the face.

I claim:

1. A continuous positive airway pressure system comprising:
    a head gear for attachment to a wearer's head comprising:
        a first ear section having an aperture for receiving a first ear, an inner edge surrounding and defining the aperture for encircling the first ear; and
        a second ear section having an aperture for receiving a second ear, an inner edge surrounding and defining the aperture for encircling the second ear;
        an attachment system extending between the first ear section and the second ear section for curving over a wearer's head; and
        a nape extension extending between the first ear section and the second ear section for curving around the nape of the neck; and
    the continuous positive airway pressure system further comprising:
        a lip strap extending between said first ear section and said second ear section over the wearer's lower lip, the lip strap having a first end looping through the aperture of said first ear section and the lip strap having a second end looping through the aperture of said second panel ear section.

2. A continuous positive airway pressure system as in claim 1, wherein the attachment system comprises a first upper extension extending from the first ear section and a second upper extension extending from the second ear section and connecting together generally midway between the first ear section and second ear section.

3. A continuous positive airway pressure system as in claim 2, wherein the first upper extension has a distal end and the second upper extension has a distal end, and wherein the first upper extension distal end is split into two straps that connect to said second upper extension distal end.

4. A continuous positive airway pressure system as in claim 3, wherein the two straps of the distal end of the first upper extension are crossed over each other and attached to the distal end of the second upper extension.

5. A continuous positive airway pressure system as in claim 1, wherein the lip strap has a center between the first end and the second end, and the system further comprising a respiratory mask for covering the wearer's nose attached to the head gear, a plurality of elongated extenders attached to the respiratory mask and each of said plurality of extenders having an extender end extending to near the center of the lip strap and a strap connecting said extender end to the headgear.

6. A continuous positive airway pressure system as in claim 2, further comprising a respiratory mask for covering the wearer's nose attached to the head gear, and wherein the mask is attached by straps extending from the mask to said first upper extension and from the mask to said second upper extension.

7. A continuous positive airway pressure system as in claim 6 wherein said first ear section, second ear section, first upper extension, and second upper extension are non-elastic.

8. A continuous positive airway pressure system as in claim 1, wherein the lip strap further has a pad of leather on an inside surface of the lip strip for contacting the wearer's lower lip.

9. A continuous positive airway pressure system as in claim 1 further comprising a respiratory mask for covering the wearer's nose attached to the head gear, wherein the respiratory mask has side edges, and the system further comprises a clip connecting the first ear section to one of said side edges, and a clip connecting the second ear section to one of said side edges.

10. A continuous positive airway pressure system comprising:
   a head gear for attachment to a wearer's head comprising:
      a first ear section having an aperture for receiving a first ear; and
      a second ear section having an aperture for receiving a second ear;
      an attachment system extending between the first ear section and the second ear section for curving over a wearer's head; and
      a nape extension extending between the first ear section and the second ear section for curving around the nape of the neck; and
   the continuous positive airway pressure system further comprising:
      a lip strap extending between said first ear section and said second ear section over the wearer's lower lip, and the lip strap having first and second ends and a center; and
      a respiratory mask for covering the wearer's nose attached to the head gear, and a plurality of elongated extenders attached to the respiratory mask and each of said plurality of extenders having an extender end extending to near the center of said lip strap and a strap connecting said extender end to the headgear.

11. A continuous positive airway pressure system as in claim 10, wherein the strap connecting said extender end to the headgear attaches to one of said first ear section and said second ear section.

12. A continuous positive airway pressure system comprising:
   a head gear for attachment to a wearer's head comprising:
      a first ear section having an aperture for receiving a first ear, an inner edge surrounding and defining the aperture for encircling the first ear, and a front portion for being positioned in front of the wearer's first ear; and
      a second ear section having an aperture for receiving a second ear, an inner edge surrounding and defining the aperture for encircling the second ear, and a front portion for being positioned in front of the wearer's second ear;
      an attachment system extending between the first ear section and the second ear section for curving over a wearer's head; and
      a nape extension extending between the first ear section and the second ear section for curving around the nape of the neck; and
   the continuous positive airway pressure system further comprising:
      a respiratory mask for covering the wearer's nose attached to the head gear, and wherein the mask is attached by a strap extending from the mask to said first ear section and by a strap extending from the mask to said second ear section; and
      a lip strap extending between said first ear section and said second ear section over the wearer's lower lip to keep the lower lip against the wearer's teeth, the lip strap having a first end and a second end, the first end attaching to the front portion of the first ear section below the strap attaching the respiratory mask to the first ear section, and the second end attaching to the front portion of the second ear section below the strap attaching the respiratory mask to the second ear section.

13. A continuous positive airway pressure system as in claim 12 wherein the attachment system comprises a first upper extension extending from the first ear section and a second upper extension extending from the second ear section and connecting together between the first ear section and second ear section, and wherein said first ear section, second ear section, first upper extension, and second upper extension are non-elastic.

14. A continuous positive airway pressure system as in claim 13 wherein said first upper extension has a distal end that is split into two straps that connect to said second upper extension.

* * * * *